United States Patent [19]

Kulprathipanja

[11] Patent Number: 5,382,747
[45] Date of Patent: Jan. 17, 1995

[54] PROCESS FOR THE ADSORPTIVE SEPARATION OF METAXYLENE FROM AROMATIC HYDROCARBONS

[75] Inventor: Santi Kulprathipanja, Inverness, Ill.

[73] Assignee: UOP, Des Plaines, Ill.

[21] Appl. No.: 110,528

[22] Filed: Aug. 23, 1993

[51] Int. Cl.$^6$ ............................................... C07C 7/12
[52] U.S. Cl. ..................................... 585/828; 585/831
[58] Field of Search .................................. 585/828, 831

[56] References Cited

U.S. PATENT DOCUMENTS 3,840,610 10/1974 Hedge ........................... 260/674 SA
4,306,107 12/1981 Broughton .......................... 585/828
4,326,092 4/1982 Neuzil ................................. 585/828

*Primary Examiner*—Anthony McFarlane
*Assistant Examiner*—Nhat D. Phan
*Attorney, Agent, or Firm*—Thomas K. McBride; John F. Spears, Jr.

[57] ABSTRACT

Metaxylene is recovered from a mixture of $C_8$ aromatic hydrocarbons including other xylenes by liquid phase adsorptive separation using a sodium or sodium and lithium exchanged Y zeolite as the adsorbent. Performance is improved by maintaining the adsorbent in a narrow range of temperature and hydration. Toluene is the preferred desorbent.

10 Claims, No Drawings

PROCESS FOR THE ADSORPTIVE SEPARATION OF METAXYLENE FROM AROMATIC HYDROCARBONS

BACKGROUND OF THE INVENTION

Field of the Invention

This invention relates to the adsorptive separation of metaxylene from a complex admixture of aromatic hydrocarbons including other xylenes. The invention more specifically relates to the recovery of metaxylene by selective liquid-phase adsorption using certain aluminosilicate zeolitic molecular sieves.

RELATED ART

Those skilled in the art are familiar with a number of adsorptive separation methods which may be employed to perform the separation of aromatic hydrocarbons. The use of zeolitic adsorbents in these methods has been well described in the literature. For instance, U.S. Pat. No. 3,840,610 issued to J. A. Hedge is directed to the adsorptive separation of a number of organic compounds such as 2,6 dimethyl naphthalene. This reference also indicates a sodium Y zeolite will separate m-xylene from p-xylene.

U.S. Pat. No. 4,306,107 issued to D. B. Broughton describes the use of a sodium containing zeolite Y and contains 2-7 wt. % water to recover metaxylene from admixture with other xylenes. Accompanying this disclosure is a discussion of the use of toluene as a desorbent, and the possibility of including silica, alumina or clay with the zeolite.

U.S. Pat. No. 4,326,092 issued to R. W. Neuzil also describes the recovery of metaxylene from xylene admixtures through the use of a sodium exchanged Y zeolite. This reference describes suitable adsorbents in terms of silica to alumina ratios and exemplifies a temperature of 150° C.

BRIEF SUMMARY OF THE INVENTION

The invention is a liquid-phase adsorptive process for separating metaxylene from a mixture containing ethylbenzene and two or more xylenes. The process employs an adsorbent comprising a zeolite Y having its ion exchange cites occupied by sodium ions or with sodium ions plus a lesser amount of lithium ions. Preferably the adsorbent is also characterized by a low water content. Indan or toluene is employed as the desorbent.

One embodiment of the invention may be characterized as a process for separating metaxylene from a mixture comprising metaxylene and at least one other $C_8$ aromatic hydrocarbon, which process comprises contacting said mixture at adsorption conditions including a temperature between about 100° and about 145° C. with an adsorbent comprising a Y zeolite containing sodium ions and having a hydration level giving an LOI as defined herein of about 1.5 to about 3.0 wt. %, selectively adsorbing metaxylene on said adsorbent, removing the nonadsorbed portion of said mixture from contact with said adsorbent and recovering metaxylene by desorption with a desorbent at desorption conditions.

DETAILED DESCRIPTION OF THE INVENTION AND PREFERRED EMBODIMENTS

Metaxylene is a valuable commercial commodity used in the manufacture of a number of useful products including insecticides and isophthalic acid. The effluent of the typical naphtha reforming zone contains a high concentration of aromatic hydrocarbons and there have been proposals to recover metaxylene from such aromatic-rich hydrocarbon mixtures by adsorption in the same manner paraxylene is now recovered. It has also been suggested to recover metaxylene from the process streams circulating in xylene isomerization units prior to or subsequent to the recovery of other desired xylene isomers. Examples of these proposals which use fractionation and crystallization are present in U.S. Pat. Nos. 3,700,744; 3,729,523 and 3,773,846. It has also been proposed to recover m-xylene by extractive distillation as described in U.S. Pat. No. 4,585,526. However, the recovery of metaxylene has not been a commercial success and much metaxylene in these sources is simply converted to other materials such as benzene or paraxylene.

The references cited above indicate that adsorptive-separation has also been considered for the recovery of metaxylene and that adsorbents have been found which will selectively separate m-xylene from admixtures containing one or both of the other xylene isomers. For instance, the combination of a sodium Y zeolite adsorbent and toluene as the desorbent as disclosed by Neuzil is believed to be suitable for this separation. However, when this system was tested in pilot plant scale operations, it was found to suffer from two disadvantages which would most likely prevent large scale commercialization. These disadvantages are (1) a need for an undesirably high ratio of the volume of adsorbent to the volume of feed stream (A/F ratio), which translates into the requirement for larger more costly commercial scale plants and (2) performance is poor in the presence of a high concentration of o-xylene, as occurs in some feed streams and in some zones of the simulated countercurrent moving bed adsorption system preferred for performing the process.

It is an objective of the subject invention to provide an improved process for the commercial scale separation of metaxylene from other $C_8$ aromatic hydrocarbons. It is a further objective to provide an adsorptive process for the recovery of meta-xylene from xylene rich hydrocarbon fractions.

These objectives are achieved through the use of a desorbent comprising a zeolite Y together with specific desorbents and process conditions. The maintenance of specific process temperature and adsorbent hydration levels are critical to completely meeting both objectives. The type Y zeolite is generally described in U.S. Pat. No. 3,130,007. The framework silica:alumina ratio of the Y zeolite used in the subject process is preferably between about 4.0:1 and about 6.0:1 and more preferably less than about 5.5:1.

In one embodiment of the invention a sodium Y zeolite is used. In a preferred alternative embodiment a minor portion of the native sodium is replaced by ion exchange with lithium ions. Exchange methods well known to those skilled in the art are suitable for the preparation of the zeolites used in this invention. It is preferred that at least about 5 mole percent of the sodium ions are replaced by lithium ions and more preferably that at least about 10 to about 15 percent of the sodium ions are replaced by lithium ions. The zeolite should contain less than 50% lithium, preferably less than 40% and most preferably less than 35% lithium ions. A suitable range of lithium exchange is therefore from about 5 to 35 and preferably about 10— about 30 mole %. Further information on the effect of lithium exchange is given in the example below. Suitable adsorbent materials are available from UOP of Des Plaines, Ill., U.S.A. and other suppliers.

Those skilled in the art will recognize that the performance of an adsorbent is greatly influenced by a number of factors not related to its composition such as operating conditions, feed stream composition, water content and desorbent composition. The optimum adsorbent composition is therefore dependent upon a number of interrelated variables.

One very important adsorbent composition variable is the water content of the adsorbent, which is expressed herein in terms of the recognized Loss on Ignition (LOI) test. For instance Broughton, cited above, reported a preference for 2–7 % water. As used herein, in the LOI test the volatile matter content of the zeolitic adsorbent is determined by the weight difference obtained before and after drying a sample of the adsorbent at 400° C. under an inert gas purge such as nitrogen for a period of time sufficient to achieve a constant weight. The difference in weight, calculated as a percentage of the sample's initial weight, after being calcined for 2 hours at 500° C., is reported as loss on ignition at 500° C. An LOI greater than 1.5% is critical to meet the objectives of the invention. It is preferred that the water content of the adsorbent results in an LOI at 500° C. of less than 3.5% and preferably within the range of from about 1.5 to about 3.0wt %. An LOI of about 2.0 to 2.5 wt % is highly preferred.

Typically, the adsorbent particles used in separation processes contain small zeolite crystals dispersed in an amorphous inorganic matrix such as alumina or clay. A clay binder comprising both silica and alumina, e.g., Minugei is preferred. The zeolite will ordinarily be present in the adsorbent particles in amounts ranging from about 75 to about 98 wt. % based on volatile-free composition. Volatile-free compositions are generally determined after the adsorbent has been calcined at 900° C. in order to drive off all volatile matter. The nonzeolitic portion of the adsorbent will generally be an inorganic matrix material which is present in intimate mixture with the small particles of the zeolite. This matrix material may be an adjunct of the manufacturing process for the zeolite (for example, from the intentionally incomplete purification of the zeolite during its manufacture) or it may be added to relatively pure zeolite, but in either case its usual function is as a binder to aid in forming or agglomerating the zeolite into hard crystalline particles, such as extrudates, aggregates, tablets, macrospheres or granules having a desired particle size range. The typical adsorbent will have a particle size range of about 16–60 mesh (Standard U.S. Mesh).

Although both liquid and vapor phase operations can be used in many adsorptive separation processes, liquid-phase operation is preferred for this process because of the nature of the materials being separated. Adsorption conditions can include a temperature range of from about 20° to about 200° C. However, temperatures of 100° to about 150° C. are needed for good results and with 100° to 145° C. being preferred. A temperature of about 120° to about 130° C. is highly preferred. Increased temperature tends to reduce retention volumes and is necessary to achieving the objectives of the invention. Adsorption conditions also include a pressure range of from about atmospheric to about 500 psig as required to insure liquid phase operations with pressures from about atmospheric to about 250 psig being preferred. Desorption conditions preferably include the same temperature and pressure as used for adsorption.

In the present invention the separation of m-xylene is effected by passing a feed mixture comprising a mixture of $C_8$ aromatic hydrocarbons over an adsorbent which selectively adsorbs the m-xylene while permitting other components of the feed stream to pass through the adsorption zone. The feed mixture can be derived from reformate or separation units as described above. Such separations are imprecise and the feed is expected to contain other compounds, such as $C_9$ aromatics, which are considered impurities. The flow of the feed is stopped and the adsorption zone is flushed to remove nonadsorbed materials surrounding the adsorbent. Thereafter the m-xylene is desorbed from the adsorbent by treating the adsorbent with a desorbent material, preferably comprising an aromatic hydrocarbon. The desorbent material is commonly also used to flush nonadsorbed materials from the adsorption zone prior to the desorption step.

For purposes of this invention, various terms used herein are defined as follows. A "feed mixture" is a mixture containing one or more extract components and one or more raffinate components to be separated by the process. The term "feed stream" indicates a stream of a feed mixture which passes to the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the desorbent. The term "raffinate stream" or "raffinate output stream" means a stream in which a raffinate component is removed from the adsorbent bed. The composition of the raffinate stream can vary from essentially 100% desorbent material to essentially 100% raffinate components. The term "extract stream" or "extract output stream" shall mean a stream in which an extract material which has been desorbed by a desorbent material is removed from the adsorbent bed. The composition of the extract stream can vary from essentially 100% desorbent material to essentially 100% extract components. At least portions of the extract stream and the raffinate stream are passed to separation means, typically fractionators, where at least a portion of desorbent material is recovered to produce an extract product and a raffinate product. The terms "extract product" and "raffinate product" mean products produced by the process containing, respectively, an extract component and a raffinate component in higher concentrations than those found in the extract stream and the raffinate stream.

The rate of exchange of an extract component with the desorbent can generally be characterized by the width of the peak envelopes at half intensity obtained from plotting the composition of various species in the adsorption zone effluent obtained during a pulse test versus time. The narrower the peak width, the faster the desorption rate. The desorption rate can also be characterized by the distance between the center of the tracer peak envelope and the disappearance of an extract component which has just been desorbed. This distance is time dependent and thus a measure of the volume of desorbent pumped during this time interval. The tracer is normally a relatively unadsorbed compound which moves through the column faster than the materials to be separated.

The rate at which one species of a mixture moves in and out of the adsorbent can also be reported in terms of a quantity referred to as stage time. Stage time is calculated based upon the half width of a component peak and serves to correct observations otherwise founded on net retention volumes of the individual species. The calculation of stage time has been described in "Principles of Adsorption and Adsorption Processes" by Douglas M. Ruthven, published by John Wiley & Sons, 1984. A shorter stage time does not indicate a component has a shorter residence time in the adsorption zone. Short stage times are however desirable in any system destined for commercialization and which therefore involve large investments for the plant, equipment and adsorbent, etc.

Selectivity, ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope.

Selectivity can be expressed not only for one feed compound relative to another but can also be expressed between any feed mixture component and the desorbent material. The selectivity, ($\beta$), as used throughout this specification is defined as the ratio of the two components in the adsorbed phase divided by the ratio of the same two components in the unadsorbed phase at equilibrium conditions. Relative selectivity may be calculated from:

$$\text{Selectivity} = \frac{\text{wt. percent } C/\text{wt. percent } D_A}{\text{wt. percent } C/\text{wt. percent } D_U}$$

where C and D are two components of the feed represented in weight percent and the subscripts A and U represent the adsorbed and unadsorbed phases, respectively. The equilibrium conditions are determined when the feed passing over a bed of adsorbent does not change composition, in other words, when there is no net transfer of material occurring between the unadsorbed and adsorbed phases.

Where selectivity of two components approaches 1.0, there is no preferential adsorption of one component by the adsorbent with respect to the other; they are both adsorbed to about the same degree with respect to each other. As $\beta$ becomes less than or greater than 1.0, there is a preferential adsorption by the adsorbent for one component with respect to the other. When comparing the selectivity by the adsorbent of component C over component D, a $\beta$ larger than 1.0 indicates preferential adsorption of component C within the adsorbent. A $\beta$ less than 1.0 would indicate that component D is preferentially adsorbed leaving an unadsorbed phase richer in component C and an adsorbed phase richer in component D.

While separation of an extract component from a raffinate component is theoretically possible when the selectivity of the adsorbent for the extract component with respect to the raffinate component is not much greater than 1, it is preferred that such selectivity approach a value of 2. Analogous to relative volatility in fractional distillation, the higher the selectivity, the easier the adsorptive separation is to perform. Higher selectivities permit a smaller amount of adsorbent to be used.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component and therefore permit a reduction in the operating cost of the process. With faster rates of exchange less desorbent material has to be pumped through the process and separated from the extract stream for reuse in the process. Ideally, desorbent materials should have a selectivity equal to about 1 or slightly less than 1 with respect to all extract components so that all of the extract components can be desorbed as a class with reasonable flow rates of desorbent material, and so that extract components can displace desorbent material in a subsequent adsorption step.

In adsorptive separation processes which are generally operated continuously at substantially constant pressures and temperatures to insure liquid phase the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component or both would complicate or prevent product recovery.

Since both the raffinate stream and the extract stream typically contain desorbent materials, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. Therefore at least a portion of the desorbent material is normally separated from the extract and the raffinate streams of an adsorptive separation process by distillation or evaporation, but other separation methods such as reverse osmosis could also be employed a[one or in combination with distillation or evaporation. Finally, desorbent materials should also be materials which are readily available and therefore reasonable in cost.

A dynamic testing "pulse test" apparatus may be employed to test adsorbents with a particular feed mixture and desorbent material to measure such adsorbent characteristics as adsorptive capacity, selectivity, resolution and exchange rate. The apparatus used herein consists of an adsorbent chamber of approximately 70 cc volume having inlet and outlet portions at opposite ends of the chamber. The chamber is contained within a temperature control means and pressure control equipment is used to operate the chamber at a constant predetermined pressure. Quantitative and qualitative analytical equipment such as refractometers, polarimeters and chromatographs can be attached to an outlet line of the chamber and used to detect quantitatively or determine qualitatively one or more components in the effluent stream leaving the adsorbent chamber. During a pulse test, the adsorbent is first filled to equilibrium with a particular desorbent material by passing the desorbent material through the adsorbent chamber. A pulse of the feed mixture, sometimes diluted in desorbent, is then injected for a duration of one or more minutes. Desorbent flow is resumed, and the feed components are eluted as in a liquid-solid chromatographic operation. The effluent can be analyzed on-stream or, alternatively, effluent samples can be collected periodically and later analyzed separately and traces of the envelopes of corresponding component peaks plotted in terms of component concentration versus quantity of effluent.

From information derived from the pulse test adsorbent performance can be rated in terms of void volume, retention volume for an extract or a raffinate component, selectivity for one component with respect to the other, stage time, the resolution between the components and the rate of desorption of an extract component by the desorbent. The retention volume of an extract or a raffinate component may be determined from the distance between the center of the peak envelope of an extract or a raffinate component and the peak envelope of a tracer component or some other known reference point. It is expressed in terms of the volume in cubic centimeters of desorbent pumped during this time interval represented by the distance between the peak envelopes.

Retention volumes for good candidate systems fall within a range set by extrapolation to commercial designs. A very small retention volume indicates there is little separation between the two components. (One material is not adsorbed strongly enough.) Large extract retention volumes indicate it is difficult for the desorbent to remove the retained extract compound. In terms of the pulse test described herein retention volumes in the broad range of 30–90 cc's are normally desired.

Valuable information about adsorbent/desorbent performance can also be obtained from a test procedure known as a reverse pulse test. This procedure can be performed using the same equipment and conditions as the standard Dulse test. The composition of the feed "pulse" and the desorbent are however different. In a pulse test for the subject adsorbent system the feed pulse contains all components of the normal feed, e.g., ethylbenzene and each of the xylene isomers (the feed need not contain all these materials). In a reverse pulse test the preferably adsorbed (extract) material is not present in the feed but is used as the desorbent. For example, in the present system the feed pulse for a reverse pulse test would contain ethylbenzene, ortho and para xylene and toluene. The desorbent would be metaxylene. The feed pulse can also contain the normal diluent or marker compounds such as nonane. Normally, low stage times are desired in a reverse pulse test.

The information provided by a reverse pulse test supplements the pulse test information by indicating the adsorbent/desorbent system performance at high concentrations of the extract material, in this case meta xylene, as occur in zones 2 and 3 of the simulated countercurrent moving bed operation described herein. These zones operate with high concentrations, e.g., 40–80% of the extract component. A meaningful difference in stage times and net retention volumes at these conditions is also needed to provide a commercial scale process which yields satisfactory performance in a reasonably sized facility, that is, meets the objectives of the invention.

In a commercial unit the adsorbent may be employed in the form of a fixed bed which is alternately contacted with the feed mixture and desorbent materials. In the simplest embodiment of the invention, the adsorbent is employed in the form of a single static bed in which case the process is not continuous. In another embodiment, a set of two or more static beds may be employed with appropriate valving so that the feed mixture is passed through one or more adsorbent beds while the desorbent materials can be passed through one or more of the other beds in the set. The flow of feed mixture and desorbent materials may be either upward or downward through the adsorbent.

Any of the conventional apparatus employed in static bed fluid-solid contacting may be used in a commercial embodiment of the process. Countercurrent moving bed or simulated moving bed countercurrent flow systems, however, have a much greater separation efficiency than fixed adsorbent bed systems and are, therefore, highly preferred for commercial installations. One such moving bed system is described in U.S. Pat. No. 4,385,993. In the moving bed or simulated moving bed processes, the adsorption and desorption operations are continuously taking place which allows both continuous production of an extract and a raffinate stream and the continual use of feed and desorbent streams.

One preferred adsorbent contacting method utilizes what is known in the art as the simulated moving bed countercurrent flow system. The operating principles and sequence of such a flow system are described in U.S. Pat. No. 2,985,589 and 3,310,486, incorporated by reference herein. In such a system, it is the progressive movement of multiple liquid access points down an adsorbent chamber that simulates the upward movement of adsorbent contained in the chamber. Typically only four of the many access lines to the chamber are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. To maintain the simulated movement, a liquid flow down the adsorbent chamber may be provided by a pump. As an active liquid access point moves through a cycle, that is, from the top of the chamber to the bottom, the chamber circulation pump provides different flow rates. A programmed flow controller may be provided to set and regulate these flow rates.

The active liquid access points effectively divide the adsorbent chamber into separate zones, each of which has a different function. It is generally necessary that three separate operational zones be present in order for the process to take place, although, in some instances, an optional fourth zone may be used. The zone numbers used in this description of a simulated moving bed process are those used and illustrated in U.S. Pat. Nos. 3,392,113 and 4,475,954 which are also incorporated herein by reference.

The adsorption zone, zone 1, is defined as the adsorbent located between the feed inlet stream and the raffinate outlet stream. In this zone, the feedstock contacts the adsorbent, an extract component is adsorbed, and a raffinate stream is withdrawn. The general flow through zone 1 is from the feed stream which passes into the zone to the raffinate stream which passes out of the zone, and the flow in this zone is considered to be a downstream direction when proceeding from the feed inlet to the raffinate outlet streams.

Immediately upstream, with respect to fluid flow in zone 1, is the purification zone, zone 2. The purification zone is defined as the adsorbent between the extract outlet stream and the feed inlet stream. The basic operations taking place in zone 2 are the displacement from the nonselective void volume of the adsorbent of any raffinate material carried into zone 2 and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet streams. The function of the desorbent zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances, an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized, the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating valve in which the input and output streams are each directed by the valve to one of the many lines connected to the adsorbent chamber and by which the location at which the feed input, extract output, desorbent input and raffinate output streams enter or leave the chamber are advanced in the same direction along the adsorbent bed. Both the manifold arrangement and disc valve are known in the art. A multiple valve apparatus is described in detail in U.S. Pat. No. 4,434,051. Rotary disc valves which can be utilized in this operation are described in U.S. Pat. Nos. 3,040,777; 4,632,149; 4,614,204 and 3,422,848. These patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which a desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of this invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by conduits. Input/output taps are attached at a number of locations with the active taps being periodically shifted to effect continuous operation.

Normally at least a portion of the extract output stream will pass into a separation means such as a fractionation column wherein a portion of the desorbent material can be recovered to produce an extract product containing a reduced concentration of desorbent material and a desorbent recycle stream. Preferably at least a portion of the raffinate output stream will also be passed to a separation means wherein a portion of the desorbent material is recovered to produce additional recycle desorbent and a raffinate product containing a reduced concentration of desorbent material. The design of such fractional distillation facilities will be dependent on the materials being separated, the desorbent composition, etc. An example for one aromatic hydrocarbon adsorptive separation process is provided by U.S. Pat. No. 5,177,295.

Another type of a simulated moving bed flow system suitable for use in the process of the present invention is the cocurrent high efficiency simulated moving bed process disclosed in U.S. Pat. Nos. 4,402,832 and 4,478,721 to Gerhold, incorporated by reference herein in its entirety. This process may be preferred, because of its energy efficiency and lower capital costs, where products of slightly lower purity are acceptable.

The size of the units which can utilize the process of this invention can vary anywhere from those of pilot plant scale (see, for example, U.S. Pat. No. 3,706,812) to those of commercial scale and can range in flow rates from as little as a few cc's an hour to many thousands of gallons per hour.

The examples shown below are intended to further illustrate the process of this invention rather than unduly limiting the scope and spirit of said process. The examples present test results for various adsorbents and conditions determined using the previously described dynamic pulse and reverse pulse test methods.

EXAMPLE A

In this series of tests the temperature was varied to determine the effect of temperature on selectivity and adsorption rates. The tests were standard pulse tests as described above performed using a 70 cc column and 2.0 cc feed pulse containing equal quantities of n-$C_9$ tracer (nonane), ethylbenzene and each of the three xylene isomers. The adsorbent was a sodium Y zeolite conditioned to an LOI of 2.0% before the test. The selectivity, net retention volume (NRV) and stage time are reported in Table A. Also reported is the stage time for o-xylene determined in a separate reverse pulse test using the same equipment and conditions.

TABLE A

| Temp °C. | Selectivity (m-xyl/o-xyl) | NRV (m-xylene) | StageTime (m-xylene) | StageTime* (o-xylene) |
|---|---|---|---|---|
| 100 | 1.89 | 15.4 | 18.9 | 37.8 |
| 125 | 1.78 | 14.6 | 14.5 | 20.5 |
| 150 | 1.65 | 13.4 | 13.7 | 15.1 |

*for o-xylene by Reverse Pulse test

This data shows both m-xylene selectivity and stage times decrease with increasing temperature. A balance between these conflicting trends must therefore be sought.

A review of the data in Table A reveals that selectivities are better at lower temperatures as shown by the selectivity at 100° C. However, the benefits of operating at lower temperatures have to be weighed against the detriment of lower temperatures. The most significant disadvantage of operating at a lower temperature is a decrease in the transfer rate (increase in stage time) of the various feed components versus the adsorbent. The decrease in transfer rates results in a broadening of the adsorption profile or envelopes of the individual components. This results in more overlap of the envelopes ("tailing" of one component into another) for any one set of conditions. An overlap of the envelope means that two or more components will be present in the portion of the extract stream subject to the overlap and the purity of the recovered streams will decrease. To compensate for this it is necessary to increase the amount of adsorbent which is used to perform the separation with the same degree of separation. This is turn increases the cost of the process.

EXAMPLE B

A series of tests was performed to measure the effects of adsorbent water content as measured by LOI at 500° C. on selectivity and transfer rates. The adsorbent was a sodium Y zeolite. The desorbent was toluene and the tests were performed at 125° C. using a 2 cc feed pulse containing equal volumes of normal C9 paraffin tracer, ethylbenzene, p-xylene, m-xylene and o-xylene in the standard 70 cc column. The results for m-xylene are reported below in Table B1.

TABLE B1

| LOI | Selectivity (m-xyl/o-xyl) | NRV (m-xylene) | StageTime (m-xylene) | StageTime* (o-xylene) |
|---|---|---|---|---|
| 0.2 | 2.05 | 17.5 | 17.6 | 41.5 |
| 1.0 | 1.99 | 17.1 | 17.2 | 34.5 |
| 2.0 | 1.78 | 14.6 | 14.5 | 20.5 |
| 3.0 | 1.51 | 12.6 | 16.8 | 22.7 |

*for o-xylene by Reverse Pulse test (m-xylene desorbent)

A second series of tests was performed at 125° C. using a Y zeolite containing 10 mol % lithium and 90 mol % sodium ions. The tests were performed with the same conditions and procedures as used with the 100% sodium sieve. The results appear in Table B2. This data indicates increasing the adsorbent LOI reduces selectivity, NRV and stage time but the reverse pulse test shows a minimum in the o-xylene stage time below 3%.

TABLE B2

| LOI | Selectivity (m-x/o-x) | NRV (m-x) | StageTime (m-x) | StageTime* |
|---|---|---|---|---|
| 0.2 | 2.16 | 18.3 | 18.0 | 22.7 |
| 2.0 | 1.91 | 16.7 | 15.8 | 26.9 |
| 3.0 | 1.69 | 14.5 | 14.7 | 14.6 |

*for o-xylene by Reverse Pulse test (m-xylene desorbent)

EXAMPLE C

In this series of pulse tests, the amount of lithium exchanged into the Y zeolite was varied in order to determine the effect of increased lithium to sodium ion ratios. The tests were performed at 125° C. at an adsorbent LOI of 2.0% using the 70 cc column and a 2.0 cc feed pulse containing n-$C_9$ tracer, ethylbenzene and the three xylene isomers. The net retention volumes and stage times for m-xylene are shown below in Table C. The adsorbent was a Y zeolite containing only sodium in addition to the lithium. The desorbent was toluene. The results are given below in Table C. Again the reverse pulse test points to optimum conditions at an intermediate test while the NRV and selectivities have steady unidirectional trends. The NRV decrease is desirable while the trend toward lower selectivity is undesirable.

TABLE C

| % Li | NRV (m-xylene) | Selectivity (m-x/o-x) | Stagetime (m-xylene) |
|---|---|---|---|
| 0 | 14.6 | 1.78 | 14.5 |
| 10 | 16.7 | 1.91 | 15.8 |
| 20 | 16.0 | 1.82 | 12.2 |
| 30 | 14.5 | 1.75 | 15.8 |

EXAMPLE D

A pulse test was performed to test the performance of indan as a desorbent. The test was performed at 90° C. at an adsorbent LOI of 2.0% using a 70 cc column and a 2.0 cc feed pulse containing ethylbenzene, nonane, and the three xylene isomers. The net retention volume for meta xylene was 19.5 and the stage time was 29.8.

The selectivity versus para and ortho xylene respectively were 1.72 and 1.93 indicating this adsorbent/desorbent combination provided a good separation. The adsorbent was a Y zeolite containing only sodium ions.

EXAMPLE E

This example compares the results obtained at the prior art operating conditions of 0.2 wt % adsorbent LOI and 150° C. with the conditions of the subject invention exemplified by a 2 wt % LOI and a temperature of 125° C. A 100% sodium Y zeolite adsorbent was used together with toluene as the desorbent. The prior art conditions resulted in a 99.4% purity at an adsorbent to feed volume ratio of 3.30. The conditions of the subject invention allowed this ratio to be reduced to 2.0 while achieving the same 99.5% purity and same recovery. This illustrates that the subject invention can greatly reduce the required size and operating cost of separation units for the recovery of meta xylene.

One embodiment of the invention may accordingly be characterized as a continuous process for separating metaxylene from a mixture comprising metaxylene and at least one other xylene, which process comprises contacting said mixture at adsorption conditions including a temperature of from about 100° to about 140° C. with an adsorbent comprising zeolite Y, which zeolite contains both lithium and sodium ions, and which comprises an amorphous binder of silica and alumina, selectively adsorbing said metaxylene, removing the nonadsorbed portion of said mixture from contact with said adsorbent and recovering metaxylene by desorption with a desorbent comprising toluene at desorption conditions.

What is claimed is:

1. A process for separating metaxylene from a mixture comprising metaxylene and at least one other $C_8$ aromatic hydrocarbon, which process comprises contacting said mixture at adsorption conditions including a temperature between about 100° and about 145° C. with an adsorbent comprising a Y zeolite containing sodium and lithium ions and having a hydration level giving a loss on ignition at 500° C. of about 1.5–3.0 wt. %, selectively adsorbing metaxylene on said adsorbent, removing the nonadsorbed portion of said mixture from contact with said adsorbent and recovering metaxylene by desorption with a desorbent at desorption conditions.

2. The process of claim 1 wherein said zeolite has a loss on ignition greater than 2.0 wt %.

3. A process for separating metaxylene from a mixture of metaxylene and at least one other xylene which comprises contacting said mixture at liquid phase adsorption conditions including a temperature between 100° and 150° C. with an adsorbent comprising a zeolite Y, which zeolite contains both lithium and sodium ions, and an amorphous binder, selectively adsorbing metaxylene on said adsorbent, removing the nonadsorbed portion of said mixture from contact with said adsorbent and recovering said metaxylene by desorption with a desorbent comprising toluene or indane at desorption conditions.

4. The process of claim 3 wherein the adsorbent has a loss on ignition of 1.5 to 3.0 wt %.

5. The process of claim 3 wherein the adsorption conditions include a temperature of from about 100° to 140° C.

6. A continuous process for separating metaxylene from a mixture comprising metaxylene and at least one xylene, which process comprises contacting said mixture at adsorption conditions including a temperature of from about 100° to about 145° C. with an adsorbent comprising zeolite Y, which zeolite contains both lithium and sodium ions, and an amorphous binder, selectively adsorbing metaxylene on said adsorbent, removing the nonadsorbed portion of said mixture from contact with said adsorbent and recovering metaxylene by desorption with a desorbent comprising toluene at desorption conditions.

7. The process of claim 6 wherein said adsorbent comprises a clay.

8. The process of claim 6 wherein said Y zeolite has from about 5 to 35 percent of its exchangeable sites occupied by lithium ions.

9. The process of claim 6 wherein the adsorption conditions include a temperature of from about 120° to about 130° C.

10. The process of claim 9 wherein the zeolite has a loss on ignition of from about 2.0 to about 2.5 wt %.

* * * * *